(12) United States Patent
Barr (10) Patent No.: US 11,850,125 B2
(45) Date of Patent: Dec. 26, 2023

(54) BANDAGE FOR MIXING SEPARATED LIQUIDS COMMUNICATED TO THE SKIN OF WEARER

(71) Applicant: Donna Marie Barr, San Diego, CA (US)

(72) Inventor: Donna Marie Barr, San Diego, CA (US)

(\*) Notice: Subject to any disclaimer, the term of this patent is extended or adjusted under 35 U.S.C. 154(b) by 629 days.

(21) Appl. No.: 17/000,242

(22) Filed: Aug. 21, 2020

(65) Prior Publication Data

US 2020/0383835 A1 Dec. 10, 2020

Related U.S. Application Data

(63) Continuation-in-part of application No. 16/326,106, filed as application No. PCT/US2019/018110 on Feb. 14, 2019, now Pat. No. 11,337,865.

(60) Provisional application No. 62/630,678, filed on Feb. 14, 2018.

(51) Int. Cl.
*A61F 13/00* (2006.01)
*A61F 13/84* (2006.01)

(52) U.S. Cl.
CPC .......... *A61F 13/00063* (2013.01); *A61F 2013/00906* (2013.01); *A61F 2013/8447* (2013.01)

(58) Field of Classification Search
USPC .................................. 424/448, 449
See application file for complete search history.

(56) References Cited

U.S. PATENT DOCUMENTS

| | | | | |
|---|---|---|---|---|
| 4,402,696 A | * | 9/1983 | Gulko | A61F 13/0226 424/448 |
| 4,666,441 A | * | 5/1987 | Andriola | A61F 13/0259 604/304 |
| 5,271,940 A | * | 12/1993 | Cleary | A61F 13/0259 424/443 |
| 11,337,865 B2 | * | 5/2022 | Barr | A61F 13/00063 |
| 2008/0274166 A1 | * | 11/2008 | Sacks | A61P 43/00 424/449 |
| 2010/0076387 A1 | * | 3/2010 | Weimann | A61K 9/7092 604/290 |
| 2012/0022474 A1 | * | 1/2012 | Adoni | A61K 9/7092 604/307 |

\* cited by examiner

*Primary Examiner* — Kim M Lewis
(74) *Attorney, Agent, or Firm* — Donn K. Harms (57) ABSTRACT

A bandage device having a flexible body with a plurality of fluid reservoirs thereon each containing a liquid topical treatment therein. Mixing areas located between the respective fluid reservoirs on the bandage provide for mixing and formation of liquid mixtures of the respective liquid topical treatments flowing thereto from the respective fluid reservoirs located adjacent thereto. The liquid mixtures from the mixing areas when absorbed through the skin of a wearer of the bandage yield an enhanced synergistic effect exceeding that of the individual fluids such medications or essential oils.

10 Claims, 7 Drawing Sheets

| Examples of OIL TYPE | GROUP A | GROUP B | GROUP C / CARRIER OIL |
|---|---|---|---|
| Aloe Vera | | | X |
| Angelica | X | | |
| Apricot Kernel | | | X |
| Bergamot | X | | |
| Camphor | X | | |
| Castor | | | X |
| Cedar wood | X | | |
| Chamomile | X | | |
| Clary Sage | X | | |
| Cypress | X | | |
| Eucalyptus | X | | |
| Frankincense | X | | |
| Geranium | X | | |
| Ginger | X | | |
| Grape seed | | | X |
| Grapefruit | X | | |
| Helichrysum | X | | |
| Jasmine | X | | |
| Jojoba Organic | | | X |
| Juniper | X | | |
| Lavender | X | | |
| Lemon | X | | |
| Lemon Balm | X | | |
| Lemon Verbena | X | | |
| Lemongrass | X | | |
| Lime | X | | |
| Litsea | X | | |
| Mandarin | X | | |
| Melaleuca | X | | |

FIG. 10

| Examples of OIL TYPE | GROUP A | GROUP B | GROUP C / CARRIER OIL |
|---|---|---|---|
| Melissa | | X | |
| Myrrh | | X | |
| Myrtle | | X | |
| Neem | | X | |
| Neroli | | X | |
| Niaouli | | X | |
| Olive Oil Extra Vrgn | | | X |
| Orange | | X | |
| Patchouli | | X | |
| Peppermint | | X | |
| Rose | | X | |
| Rosemary | | X | |
| Rosewood | | X | |
| Sage | | X | |
| Sandlewood | | X | |
| Scotch Pine | | X | |
| Spearmint | | X | |
| Sweet Basil | | X | |
| Sweet Fennel | | X | |
| Sweet Marjoram | | X | |
| Tangerine | | X | |
| Tea Tree | | X | |
| Vetiver | | X | |
| Wintergreen | | X | |
| Witch Hazel | | | X |
| Yarrow | | X | |
| Ylang-Ylang | | X | |

BANDAGE FOR MIXING SEPARATED LIQUIDS COMMUNICATED TO THE SKIN OF WEARER

1. FIELD OF THE INVENTION

This application is a Continuation in Part Application to U.S. patent application Ser. No. 16/326,106 filed on Feb. 15, 2019, which is a National Phase Patent Application based on International Application Number PCT/US19/18110 filed on Feb. 14, 2019, which claims priority to U.S. Provisional Patent Application No. 62/630,678 filed on Feb. 14, 2018, all of which are incorporated herein in their entirety by this reference thereto.

The present invention relates generally to the communication of one or a plurality of liquids into the skin of a user, such as medications, supplements, or for example, essential oils and/or carriers therefor. Such liquid communication and absorption is accomplished through the provision of an adhesive bandage configured with a plurality of reservoir sections from which liquid placed therein flows only to adjacent mixing areas of the bandage, where mixtures of adjacent liquids contact the skin of the user in a synergistic action exceeding that of the individual liquids.

2. PRIOR ART

Background of the Invention

The application of fluids and ointments and supplements such as essential oils, medications, and other topically applied liquids has been a favored manner to impart beneficial health supplements and medications to such users for many years. Unfortunately, such liquid medications, supplements, and especially essential oils can have odors which may be found less than pleasant by users and bystanders, and such liquids providing topical treatments can also stain clothing and cause other undesirable issues.

The device and system herein provides for an ongoing communication of separate supplies of liquids to the skin and body of the user in a fashion protecting the clothing and person of the user from the damage and undesirable aspects of such fluids. Additionally, mixtures of such fluids such as medications or supplements such as essential oils and/or carriers therefor to assist in communication through the skin of the user, provide a synergistic effect in treatment which exceeds that of either of the individual liquids.

The forgoing examples of related art as to the topical application of liquids for medication and supplements, such as the employment of essential oils and other liquids for treatment of illness and health benefits, and limitations related therewith, are intended to be illustrative and not exclusive, and they do not imply any limitations on the invention described and claimed herein. Various limitations of the related art will become apparent to those skilled in the art upon a reading and understanding of the specification below and the accompanying drawings.

SUMMARY OF THE INVENTION

The present invention overcomes the shortcomings of the prior art in the employment of liquid topical treatments as supplements or medications for health conditions. By topical treatment is meant a liquid which is absorbed through the skin of the user which is employed as a medication and/or health supplement and/or a treatment for a skin and/or bodily health condition.

For example, such topical treatments may be medications such as antibiotics or topical medications sold commercially, or in a preferred mode of the system herein, such supplements can be essential oils and other liquids absorbed through the skin for treatment of health issues and for health benefits. The system employing the bandage device herein, provides a wearable bandage having a flexible body configured to hold a plurality of reservoirs supplying such topical treatments in the form of liquids adapted for application to and through the skin surface of a user, to which the bandage removably attaches.

The device herein, in the preferred mode, includes a body formed of a flexible substrate material, such as vinyl or another polymeric material which will preferably stretch and removably adhere to the skin surface of a user. A first side surface of the body of the bandage has adhesive thereon positioned to hold the bandage upon the skin of the user for a duration of time. Such adhesive is preferably positioned around the perimeter edge of the first side of the body of the bandage to form a sealed engagement of the first surface of the body of the bandage adjacent the skin of the user.

Additionally, positioned on the first side surface of the body of the flexible bandage is a plurality of liquid reservoirs which are fluidly separated from each other and which are positioned to have a mixing area located therebetween. By plurality of liquid reservoirs is meant at least two such reservoirs adapted to hold a supply of liquid topical treatments therein and can communicate a fluid flow therefrom into an adjacent mixing area which is formed on the first side surface, in between the plurality of liquid reservoirs. Such reservoirs can be pre-loaded with the different liquids at the factory, or the bandage device can be supplied with a porous one-way membrane covering the reservoirs thereby allowing the user to load each with the topical liquid of choice.

The mixing areas may be surface areas of the first side surface of the body of the bandage running in between the adjacent reservoir areas wherein fluid flows of topical treatments communicate in respective fluid streams from adjacent reservoir areas. In each such mixing area on the first side surface of each body of such a bandage, the communicated fluid streams of individual liquid topical treatments will mix to form a liquid mixture. By liquid topical treatment is meant any supplement, medication, or other topically applied liquid which may be placed in one of the reservoirs and which will flow thereafter into an adjacent mixing area. By liquid mixture is meant any two liquid topical treatments which combine in a respective mixing area to form a liquid mixture of the two. Thus, each mixing area will yield a liquid mixture therein from the first liquid topical treatment flowing thereto from a first reservoir area and a second liquid topical treatment flowing thereto from a second reservoir area adjacent the mixing area.

While medications such as antibiotics or other topically applied medications and essential oils are taught herein as a particularly preferred type of topical treatments, such should not be in any fashion limiting in scope. The synergistic effect of the mixing in mixing areas of a plurality of such liquid topical treatments is achievable with an infinite number of such liquid topical treatments which may be combined and such is anticipated within the scope of this application.

The formed liquid mixture or mixtures within one or a plurality of mixing areas will be absorbed into the skin of the user in communication with the mixing areas. Alternatively, absorbent material such as gauze or gel or woven or non woven fabric material may be located in the mixing areas and mix the absorbed liquid topical treatments from adjacent reservoirs into a formed liquid mixture by a capillary action.

By absorbent material is meant woven, unwoven, extruded, or otherwise formed material which is adapted to absorb fluid communicated thereto.

The second side surface of the body of the bandage is configured to prevent the liquid topical treatment held in any of the plurality of liquid reservoirs located on the first side surface from leaking or otherwise communicating through or from the bandage. Currently, such a leakproof configuration is provided by forming the body of the bandage in a continuous elongated liquid proof substrate. Thus, liquid held in the liquid reservoir areas positioned on the first side surface will not leak through the body of the bandage, nor can it leak past the adhesive holding the perimeter edge of the first side surface of the body of the bandage to the skin of the user.

However, the body of the bandage can also be formed with means for communication of air through the body, such as by using apertures therein covered with a fluid-proof membrane having air passages therein, which are smaller than the molecules of fluid. Such will allow air to communicate through apertures in the body of the bandage and the membrane air passages and into the mixing areas but will prevent fluids therein from communicating through the membrane and body of the bandage.

As noted herein, the liquid topical treatments positioned in the individual segregated reservoir areas is beneficial to the health of the user when applied to the skin surface and/or may also provide a topical treatment for a skin condition. Further, while individual liquid topical treatments such as medications or individual essential oils have been found in experimentation to yield health benefits as topical treatments to users, the mixing of such medications or such essential oils in mixture areas located to receive topical treatment fluid flow from adjacent fluid reservoirs has been found to yield a synergistic effect once mixed. This synergistic effect provides such mixed topical treatments and health benefits to the user which have been found to exceed that of the individual liquid components.

As such, in all preferred modes of the system herein, at least one mixing area is positioned in between a plurality of adjacent reservoir areas, each of which hold a respective liquid topical treatment. These reservoir areas are configured to hold a fluid supply therein of such a liquid topical treatment and communicate a fluid stream thereof into the mixing area over a duration of hours or days while the bandage is worn. Thus, where two reservoirs are adjacent a mixing area, the first will have a liquid supply of a first topical treatment and the second reservoir will have a liquid supply of a second topical treatment.

As noted, the individual fluid reservoirs positioned on the first side surface of the body of the bandage are adapted to hold the fluid supply of a respective topical treatment therein, and disburse such in a fluid stream to a defined mixing area adjacent one or more side edges of a fluid reservoir. Such fluid reservoirs may be formed of a hollow void within a polymer layer, or in a gel, or woven fabric, or an unwoven fabric, or may be formed in any other configuration which will provide a fluid reservoir to hold or absorb fluid and thereafter communicate a fluid flow of the retained fluid in a fluid stream to the adjacent mixing area. They may also be formed with a fluid permeable surface adapted for fluid flow into the reservoir but preventing reverse flow to allow users to load their own respective liquid topical treatments to reservoirs adjacent a mixing area. For example, a membrane layer such as is used with disposable diapers can be employed to allow fluid loading to reservoirs but substantially preventing fluid flow from anywhere but defined fluid passages adjacent the mixing areas.

As another example, the reservoir may be a polymeric or similar material such as polyethylene or any other polymeric material adapted to the task, which surrounds an internal cavity. Apertures defining passages formed in one side of the polymeric material, are positioned adjacent to and only allow a flow of the liquid topical treatment into the mixing area. Where an absorbent material is employed within the reservoir, such as textile fabric or gel or other such materials which will hold fluid therein, a polymeric membrane or covering layer may be employed over the absorbent material. The polymeric covering layer will have fluid passages therein which only allow a fluid stream from the internal reservoir directly to the mixing area thereby providing an ongoing flow thereto. By polymeric material is meant any substrate formed of flexible material which is substantially impervious to fluid flow therethrough, except through fluid pathways formed therein, such as apertures.

In the system herein, employing the disclosed bandage having fluid flows of individual topical treatments from reservoirs into mixing areas, it is preferred that at least two liquid topical treatments are communicated into any mixing area in order to provide the synergistic effect of the mixture when absorbed into the skin of the user. Where medications or liquid supplements or other medical treatments are provided, in all modes it is preferred that a first reservoir area will disburse a first liquid topical treatment to the mixing area and the second reservoir area will disburse a fluid flow of a second liquid topical treatment only to the mixing area, to thereby form a liquid mixture of the two for absorption in the skin of the user.

As another example, a mixture of first topical treatment and second liquid topical treatment may include at least one essential oil from a first grouping of essential oils, and one essential oil from a second grouping of essential oils and/or one essential oil from a third grouping of essential oils.

While to be considered in no way limiting, currently a first grouping of essential oils include at least one of Angelica, Bergamot, Camphor, Cedar wood, Chamomile, Clary Sage, Cypress, Eucalyptus, Frankincense, Geranium, Ginger, Grapefruit, Helichrysum, Jasmine, Juniper, Lavender, Lemon, Lemon Balm, Lemon Verbena, Lemon grass, Lime, Litsea, Mandarin and Melaleuca.

Also in no way limiting, a second grouping of essential oils includes at least one of Melissa, Myrrh, Myrtle, Neem, Neroli, Niaouli, Orange, Patchouli, Peppermint, Rose, Rosemary, Rosewood, Sage, Sandlewood, Scotch Pine, Spearmint, Sweet Basil, Sweet Fennel, Sweet Marjoram, Tangerine, Tea Tree, Vetiver, Wintergreen, Yarrow, and Ylang-Ylang.

In an additional non limiting example, a third grouping of essential oils have been found to provide enhanced carriers which impart an enhanced communication through the skin of the user when applied thereon. This enhanced communication inures to any essential oil mixed with the carrier essential oils in this third grouping. This third grouping of essential oils includes at least one of Aloe Vera, Apricot Kernel, Castor, Grape seed, Jojoba, Olive Oil, and Witch Hazel.

Thus, where the two liquid topical treatments include one or more essential oils from the first grouping and/or the second grouping of essential oils, the two topical treatments are combined in a mixing area with at least one of the third grouping of essential oils, in addition to the synergistic effect provided by the combination mixed in the mixing area, an enhanced communication of the mixture is provided by the inclusion of one or more essential oils from the third grouping.

Thus, in all modes of the system herein, employing the bandage device herein, an enhanced liquid mixture for topical application to the skin is achieved which has a synergistic effect from combinations of two liquid topical treatment supplies such as essential oils from the noted groupings. The liquid mixture formed in the mixing area is adapted to provide medical and/or health benefits to the user and/or to treat a skin condition or body health issue.

With respect to the above description, before explaining at least one preferred embodiment of the herein disclosed essential oil combination system in detail, it is to be understood that the invention is not limited in its application to the details of mixture and formation and the method of employment of the composition herein, or in the following description or illustrated in any drawings. The synergistic effect from the combinations of essential oils and/or carrier ingredients herein described and disclosed in the various modes and combinations is also capable of other embodiments and of being practiced and carried out in various ways which will be obvious to those skilled in the art. Any such alternative formulation as would occur to those skilled in the art is considered within the scope of this patent. Also, it is to be understood that the phraseology and terminology employed herein are for the purpose of description and should not be regarded as limiting.

As such, those skilled in the art will appreciate that the conception upon which this disclosure is based, may readily be utilized as a basis for designing other bandages with mixing areas which form compositions having a synergistic effect when absorbed through the skin. It is important, therefore, that the claims be regarded as including such equivalent construction and methodology insofar as they do not depart from the spirit and scope of the present invention.

BRIEF DESCRIPTION OF DRAWING FIGURES

The accompanying drawings, which are incorporated herein and form a part of the specification, illustrate some, but not the only or exclusive examples of bandage embodiments and/or the multiple liquid topical treatments of medicines, or natural treatments such as topically applied essential oils and method herein. It is intended that the embodiments and figures disclosed herein are to be considered illustrative rather than limiting. In the drawings.

Other aspects of the disclosed bandage and system for combining essential oils for topical absorption by a user will be more readily understood when considered in conjunction with the accompanying drawings and the following detailed description, neither of which should be considered limiting.

DETAILED DESCRIPTION OF THE INVENTION

The disclosed system herein as noted in all preferred modes, includes a bandage device 10 having a body 12 which upon a first side 14 of the body 12 is positioned at least two reservoir areas 16 adjacent a mixing area 18 therebetween. In the various views provided herein, which should not be considered limiting, the separated fluid reservoir areas 16 are also designated as S1, S2, S3, and S4, depending on the number in the plurality of reservoir areas 16 positioned on the first side 14 of the body 12 of the bandage device 10.

The body 12 of the bandage device 10 is formed of elastic material such as a polymeric material and preferably has adhesive 20 positioned on the first side 14 which surrounds the perimeter of the body 12 of the bandage and the outside edges of the plurality of reservoir areas 16. Packaging of the body 12 of the bandage device 10 can include a peel-off cover (not shown) in a conventional fashion for such bandages.

Figure 1:
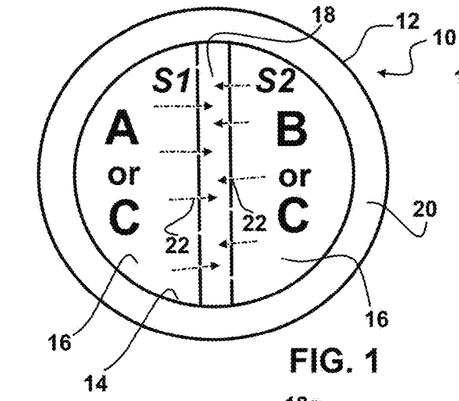
FIG. 1 depicts the bandage device herein in a mode having two reservoir areas for holding first and second liquid topical treatments on a first side surface and showing a mixing area therebetween.

As depicted in FIG. 1, the bandage device 10 herein is shown in a simplest mode having a plurality of two reservoir areas 16 located on the first side 14 of the body 12. The mixing area 18 is located therebetween.

As shown in FIG. 1 and other figures and typical to all modes of the bandage device 10 herein fluid passages 22 are positioned on the reservoir areas 16 in positions which communicate individual fluid flows only into the mixing area 18 in between adjacent reservoir areas 16. In this fashion, the reservoir areas 16 which hold an internal fluid supply of one of the groupings of essential oils noted herein, only communicate that respective essential oil held in the reservoir area 16, to the adjacent mixing area 18. With adjacent such reservoir areas 16 formed with such fluid passages 22 in positions to only communicate fluid streams to adjacent mixing areas 18, the mixing of the two different essential oils in each adjacent reservoir area 16 is ensured and the result is a synergistic effect of the mixture once absorbed into the skin of the user which communicates with a respective mixing area 18.

In FIG. 1 is shown that the adjacent reservoir areas 16, may communicate their respective fluid flows through fluid passages 22 to the mixing area 18. Each respective reservoir area 16 (S1 and S2), in the mode of FIG. 1, will hold a liquid topical treatment therein where a first liquid topical treatment and second liquid topical treatment are stored in separate reservoir areas. For example, two different liquid medications or two different essential oils from a different one of the three groupings of essential oils noted herein and shown in FIGS. 10-11.

Figure 2:
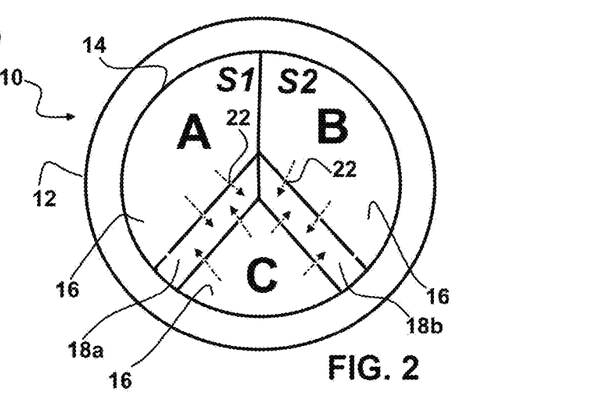
FIG. 2 depicts the bandage device herein in a mode having a plurality of three reservoir areas for holding liquid supplies of a first, second, and third liquid topical treatment on a first side surface and having a respective mixing area located therebetween.

Similar in configuration to the device 10 of FIG. 1, as shown in FIG. 2, the bandage device 10 herein may have a plurality of more than two reservoir areas 16. As shown in FIG. 2, three reservoir areas 16 are provided each of which would hold a different liquid topical treatment herein. Thus, the configuration of FIG. 2 allows for a first liquid topical treatment, a second liquid topical treatment, and a third liquid topical treatment to be loaded to respective reservoir areas 16.

As with all modes of the device 10 such liquids deposited to the plurality of reservoir areas 16, may be different liquid medications, or supplements, or in a natural mode may be one or more essential oils. Where essential oils are employed, one would be from a first grouping noted above shown as A, one or more essential oils from a second grouping of essential oils noted above and shown as B, and one or more essential oils from a third grouping of essential oils noted above and shown as C. Two mixing areas 18a and 18b are formed in between the three individual reservoir areas 16 whereby the liquid medication, supplements, essential oils, or other topically applied liquids placed in the reservoir areas 16 are mixed to respective first and second liquid mixtures for absorption to the skin.

Figure 3:
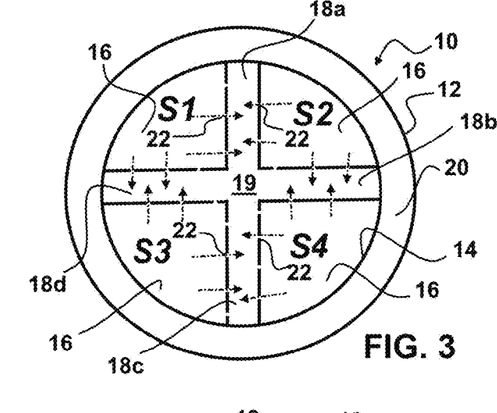
FIG. 3 shows the bandage device herein in a mode having a plurality of four reservoir areas capable of holding two, three, or four different liquid topical treatments therein on a first side surface, with a respective mixing area located therebetween.

In FIG. 3 is shown the bandage device 10 herein in a mode having a plurality of four reservoir areas 16 (S1-S4) on a first side surface 14 of the body 12 of the bandage device 10. As shown, four mixing areas 18a, 18b, 18c, and 18d, are respectively located in between each of the adjacent four reservoir areas 16, thereby forming four respective individual mixing areas 18. In each of the four mixing areas 18a-18d, a different mix of liquid topical treatments from adjacent reservoir areas 16 may be formed when communicated to the respective mixing area 18a-18d. Additionally shown is a secondary mixing area 19 which is in fluid communication with all four of the mixing areas 18a-18d which allows for the respective formed liquid mixture combinations from each of the four mixing areas 18a-18d to recombine therein to a fifth liquid mixture.

As with all modes of the device 10 herein, adjacent reservoir areas 16, if soaked with liquid essential oils, the various reservoir areas 16 preferably have essential oils held therein from a different one of the three groupings of essential oils noted above and shown in FIGS. 10-11 to ensure a mixing thereof in a respective mixing area 18 and resulting in a synergistic effect. If medications or other liquid supplements or the like are employed, a plurality of such can mix and provide this synergistic effect.

Figure 4:
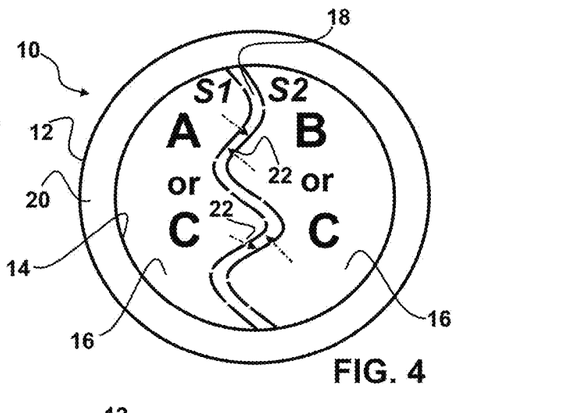
FIG. 4 depicts the bandage device herein in a mode having two reservoir areas on a first side surface similar to that of FIG. 1, but with a curvilinear enlarged mixing area formed by the curved edges of each reservoir.
Figure 5:
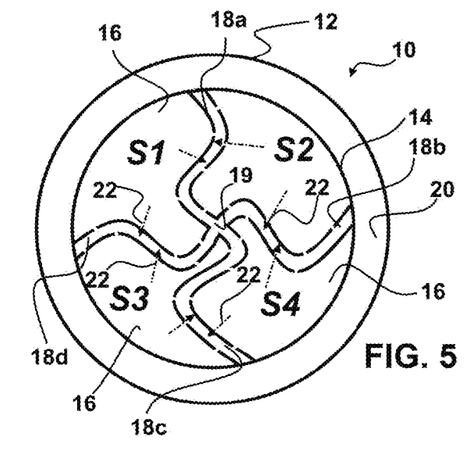
FIG. 5 depicts the bandage device herein in a mode having a plurality of four reservoir areas on a first side surface similar to that of FIG. 3 but with curvilinear enlarged mixing areas formed by the adjacent curved edges of each reservoir.

FIG. 4 shows an especially preferred mode of the bandage device 10 herein which as with FIG. 5, has curvilinear shaped mixing areas 18 formed between the adjacent reservoir areas 16 (S1 and S2). By curvilinear is meant that the mixing area 18 follows a path between a first end and second end thereof, which is serpentine or has multiple curves of the mixing area along that path. The forming of the mixing area 18 in this curvilinear configuration, where the mixing area 18 curves in between side edges of the adjacent reservoir areas 16, forms a significantly larger mixing area 18 than that of the linear mixing areas of FIG. 1, for example. This provides a larger area for the mixing of the different liquid topical treatments, such as medicines or essential oils, to yield the synergistic effect and larger area for absorption thereof on the skin of the user.

FIG. 5 as noted, shows a bandage device 10 in a mode having a plurality of four reservoir areas 16 (S1-S4) on the absorbent pad or gauze or other materials positioned on the first side surface 14 similar to that of FIG. 3. Currently, woven or non woven material formed of fibers which are made from 20-50% wood pulp, and 50-80% polymeric material such as polyester or polyethylene, has shown in experimentation to work well to hold liquids in a reservoir between fibers, and allow a flow thereof toward a mixing area 18. A membrane 24 covering the plurality of reservoir areas 16 which allows in inbound flow of liquid but substantially prevents backflow is preferred to thereby insure the mixture contacting the skin of a user only communicates to the skin in a mixing area 18.

As shown, the four mixing areas 18a-18d are formed in a curvilinear configuration defined by the adjacent curved side edges of each respective reservoir area 16. As shown, the fluid passages 22 from the adjacent reservoir areas 16 only communicate liquid essential oils held therein to the respective mixing area 18a-18d adjacent thereto. The fluid passages may also be formed by, or augmented by capillary action of the liquids flowing through a fabric or polymeric, or other pad forming the reservoir areas.

Figure 6:
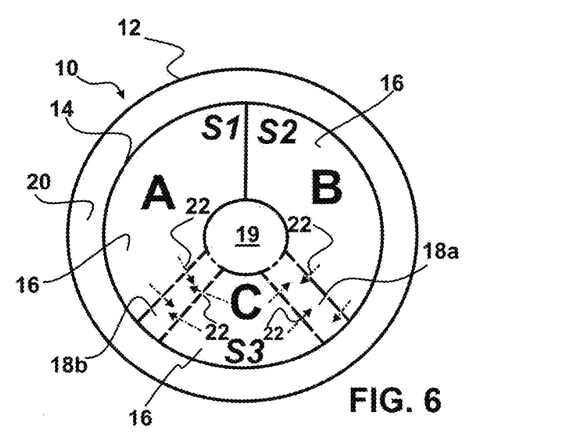
FIG. 6 depicts the bandage device herein in a mode having a plurality of three reservoir areas on a first side surface with a respective mixing area located therebetween similar to that of FIG. 2.

As with the mode of FIG. 3 and FIG. 6, the secondary mixing area 19 allows for a secondary mixture of the individual formed mixtures of essential oils communicated thereto from mixture areas 18a-18d. Thus, the user may be imparted with four liquid mixtures of medications and/or supplements and/or individual essential oils from adjacent reservoir areas 16 (S1-S4) in individual fluid communications from the mixture areas as well as a combined secondary mixture of essential oils formed in the secondary mixture area 19.

Shown in FIG. 6, is the bandage device 10 similar to that of FIG. 2, but having a centrally located secondary mixing area 19, where fluid from two adjacent mixing areas 18 flows to a secondary mixing of the already mixed fluids from the communicating adjacent mixing areas 18.

As noted above, the synergistic effect from the already mixed fluids flowing from communicating mixing areas 18a and 18b which are in fluid communication with the secondary mixing area 19, is enhanced again, when the previously combined essential oils are recombined in the secondary mixing area 19. Such a secondary mixing area 19, as noted above, may also be provided in the modes of the device 10 shown in FIGS. 3 and 5, whereupon mixed essential oils from four different respective mixing areas 18a-18d can communicate into the secondary mixing area 19 for a recombination to a secondary mixture therein.

Figure 7:
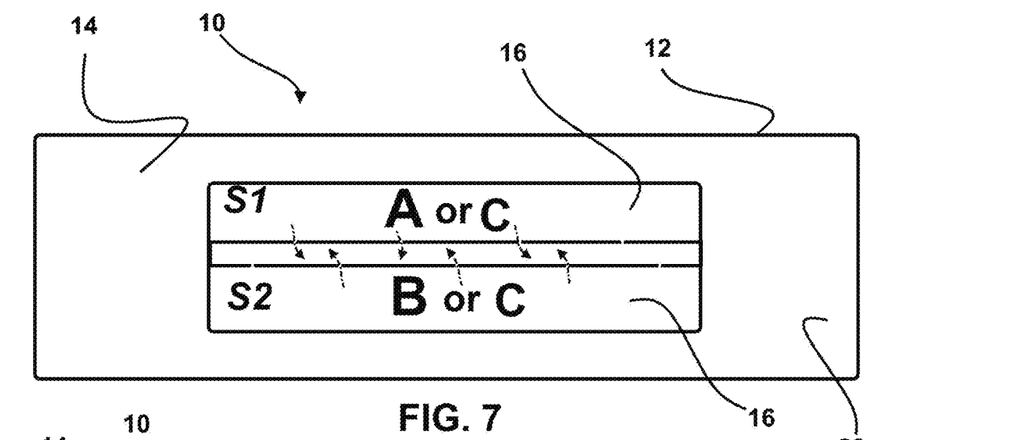
FIG. 7 shows the bandage device herein in an elongated rectangular configuration and two reservoir areas for two different liquid topical treatments on a first side surface with a mixing area therebetween.

In FIG. 7 is shown the bandage device 10 herein in an elongated rectangular configuration to show that the shape is not limited to that shown in FIGS. 1-6 and that any shape of the bandage device 10 is considered within the scope of this invention so long as it has at least two reservoir areas 16 (S1-S2) on a first side surface 14 of the flexible body 12 which form at least one mixing area 18 therebetween. The reservoir areas 16 may be formed by sections of a pad type material adapted to hold liquid and allow capillary and other flow to the mixing area 18 from individual reservoir areas 16 located on the pad. Such pad materials are well known, for example, gauze material used in bandages, and felt material and the like.

Figure 8:
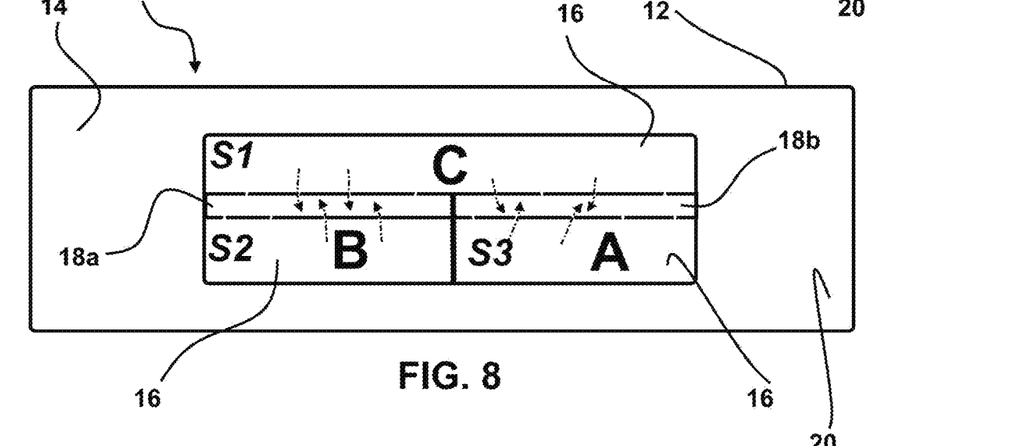
FIG. 8 depicts an elongated rectangular mode of the bandage device herein in a mode similar to FIGS. 2 and 6, having a plurality of three reservoir areas on a first side surface with a respective mixing area located therebetween.

FIG. 8 is provided to show another elongated rectangular mode of the bandage device 10 herein in a mode similar to FIGS. 2 and 6. As shown in rectangular form but in no way limiting, the bandage device 10 has a plurality of three reservoir areas (S1-S3) on the first side surface 14 with respective first and second mixing areas (18a-18b) located therebetween. The fluid passages 22 from the adjacent reservoir areas 16 communicate only into the adjacent mixing area 18a-18b located in-between other adjacent reservoir areas 16.

Figure 9:
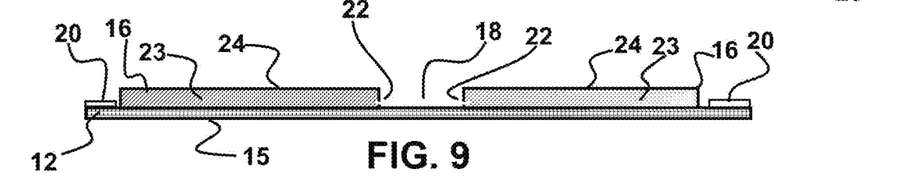
FIG. 9 shows a typical mixing area located between adjacent reservoir areas formed by a membrane with fluid passages and depicts the adhesive surrounding the perimeter edge of the body of the bandage.

In FIG. 9 is shown a sectional view through the body 12 of the device which depicts a typical mixing area 18 located between adjacent reservoir areas 16. The reservoir areas 16, as noted, are located upon a first side 14 of the body 12 opposite a second side 15 and hold fluid within an internal cavity 23 surrounded and defined by a fluid proof membrane 24. Fluid passages 22 provide a fluid flow through the membrane 24 directly to the adjacent mixing area 18 so as to allow the different fluids within reservoir areas 16, adjacent to a respective mixing area 18, to combine.

The mixing area with the bandage device 10 in an as-worn position adhesively engaged to the skin of a user, communicates the mixed fluids therein to the skin of the user. This configuration is the same where multiple mixing areas 18 are positioned on the first side 14 of the body 12 of the device 10. The body 12, as noted, is formed of a flexible material which prevents communication of fluid therethrough to the second side 15 such as vinyl or plastic or other polymeric material conventionally employed with bandages.

Figure 9A:
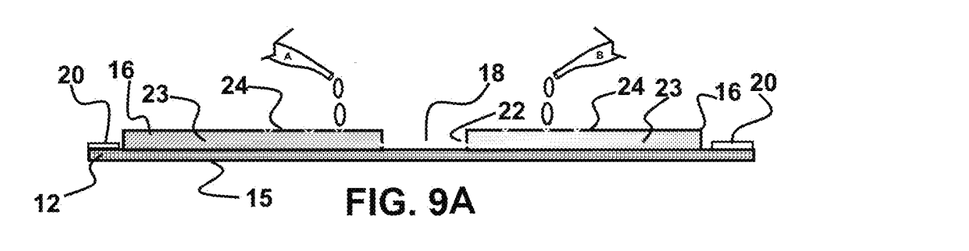
FIG. 9A depicts a mode of the device wherein the plurality of reservoir areas are configured for a user to load individual liquid topical treatments therein which will flow to form a liquid mixture in a mixing area through the fluid passages.

FIG. 9A shows a preferred mode of the device of FIGS. 1-9, wherein the plurality of reservoir areas 16 are configured for a user to load individual liquid topical treatments therein. As shown, a first liquid topical treatment A is loaded to a first of the reservoir areas 16 and a second liquid topical treatment is loaded to the second reservoir area 16. The mixing area 18 is located in between and the first liquid topical treatment and second liquid topical treatment will both flow through respective fluid passages 22 such as by capillary action through gauze or felt or other liquid-holding material forming the reservoir areas 16, into the mixing area 18, to form a liquid mixture which will be communicated to and absorbed by the skin of the user.

As shown, the membrane 24 forming the wall of the reservoir areas 16 is configured to allow one-way fluid flow into the internal cavity 23 whereupon it will flow to the fluid passages 22. The internal cavity 23 may be hollow or may be filled with gauze, felt, or other textile material, or gel or other material which will absorb the liquid topical treatment, and allow it to flow to the fluid passages 22. For example, woven and non-woven textile fabrics or felt, or cellulose or gel can be positioned in the internal cavity 23 and cause a wicking action of the fluids to the fluid passages 22.

The membrane 24 may have openings therethrough which allow ingress of the liquid topical treatment applied, but will substantially prevent outflow therethrough, such as that employed on disposable diapers. By substantially preventing outflow is meant that no more than minor amounts, if any, of the liquid topical treatment will outflow through the membrane such as 5-10 percent. However, many polymeric and textiles are employable which will allow flow into the internal cavities 23 but prevent outflow therefrom except through the fluid passages 22.

Figure 10:
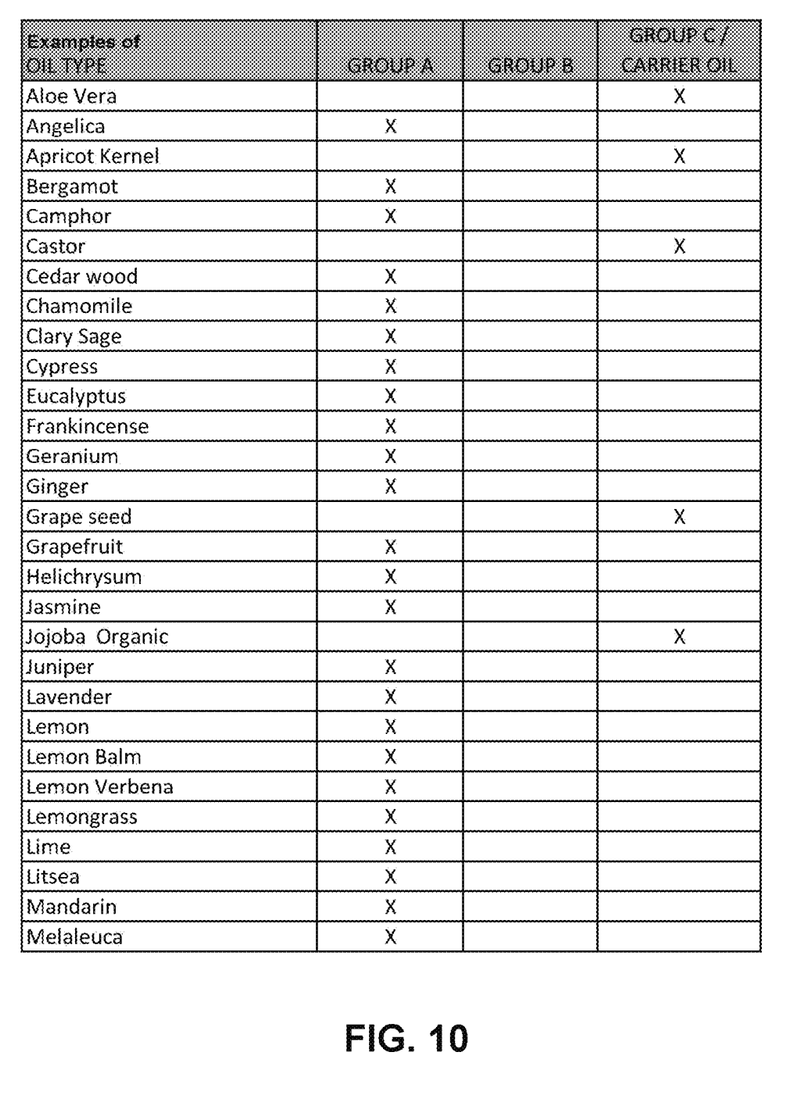
FIGS. 10-11 depict examples of currently preferred individual groupings of essential oils which when combined herein in mixing areas yield an enhanced synergistic effect when absorbed into the skin of the user exceeding that of either of the individual essential oils.
Figure 11:
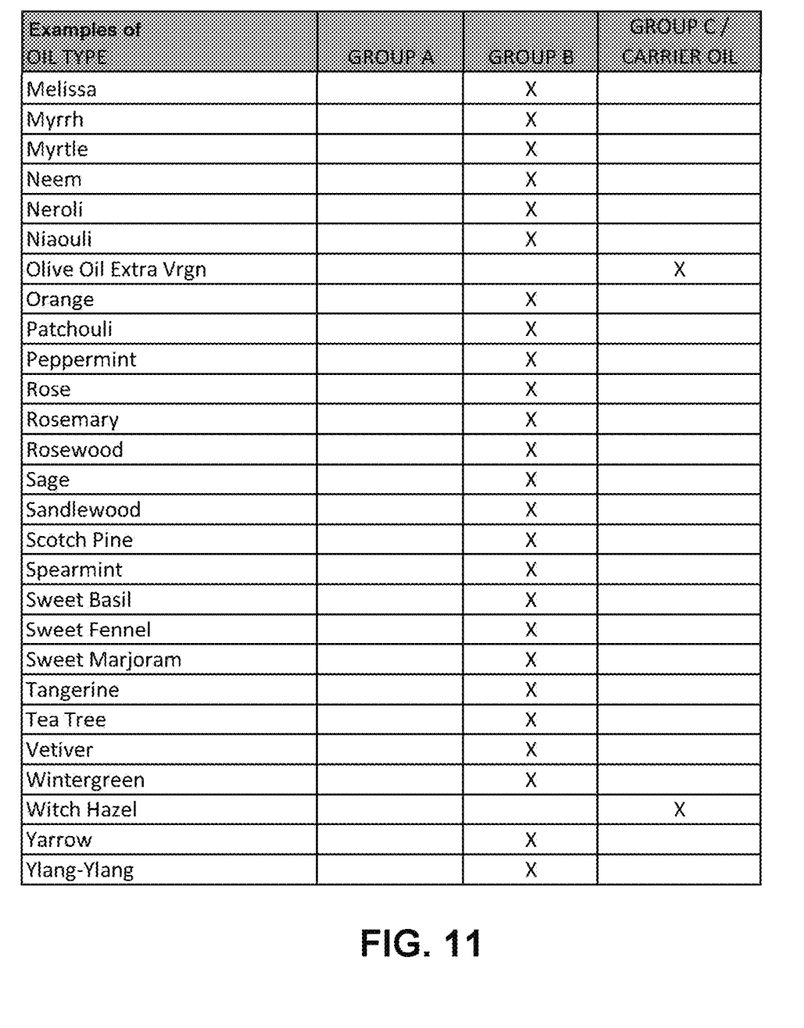

Shown in FIGS. 10-11, are the currently employed individual groupings of liquid topical treatments such as essential oils which, when combined to a liquid mixture in one or a plurality of mixing areas 18 and secondary mixing areas 19, yield an enhanced synergistic effect to the user when absorbed into the skin of the user exceeding that of either of the individual essential oils. However, the depicted liquid topical treatments in FIGS. 10-11 are only for example and as noted above, the bandage device 10 is employable with any medication, supplement, or other topical treatment which is available in liquid form which will flow through the fluid passages 22. Further, as noted above, the bandage device 10 may be provided pre-loaded with a plurality of liquid topical treatments in formed reservoir areas 16 adjacent mixing areas 18, or may be provided without pre-loading whereby the user may place their chosen or prescribed liquid topical treatments in the plurality of respective reservoir areas 16.

Figures 12, 13, 14, 15:
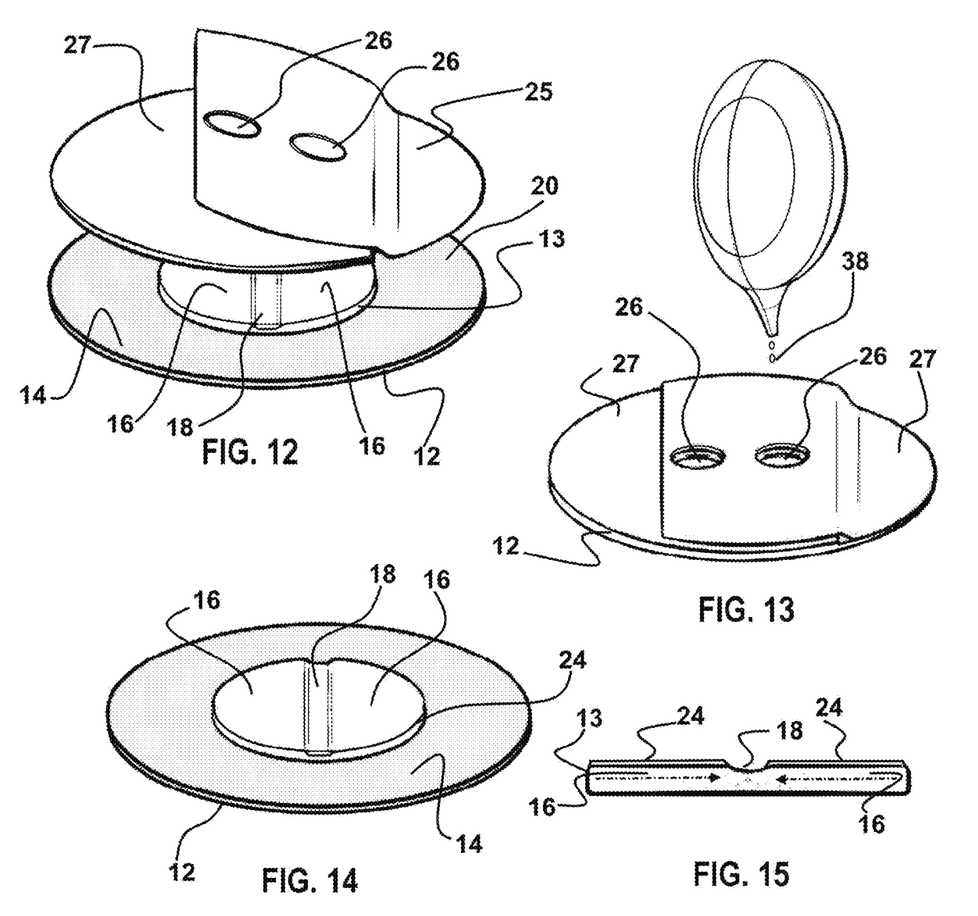
FIG. 12 depicts another preferred mode of the device herein shown in an exploded view with the wrapper such as shown in FIG. 18, removed.
FIG. 13 depicts the deposit of liquid through a plurality of openings communicating with reservoir areas of a pad positioned on a first surface of the body.
FIG. 14 shows the devices of FIGS. 12 and 13 with the removable portions having openings removed.
FIG. 15 depicts a typical pad forming the reservoir areas having a membrane on a side contacting the skin of a user and depicting the fluid flow toward a mixing area.
Figures 17, 18:
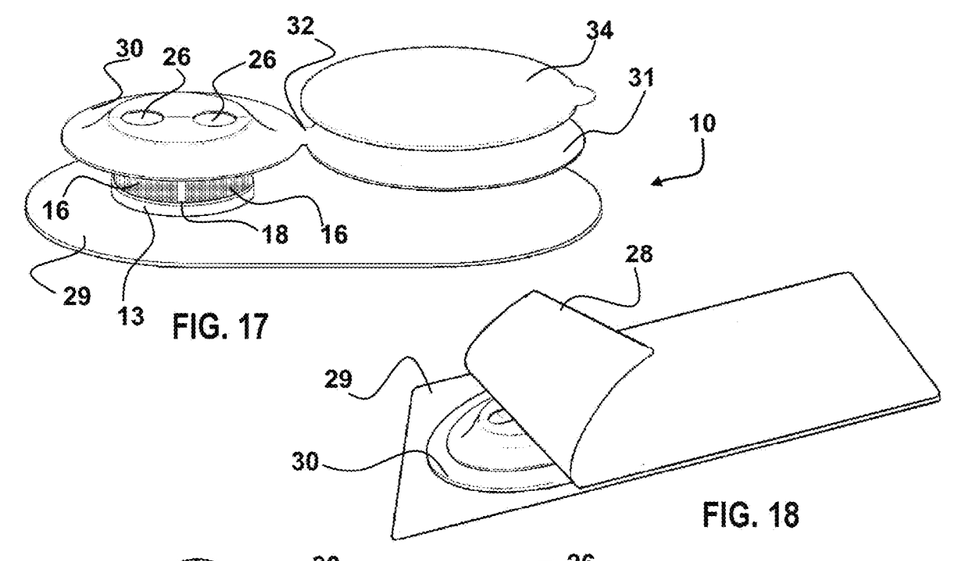
FIG. 17 shows another preferred mode of the device herein in an exploded view, where the body is formed of a first portion and second portion which are in a hinged engagement.
FIG. 18 shows a removable wrapper which would preferably be employed with all modes of the device herein.

Shown in FIG. 12 is another preferred mode of the device 10 shown in an exploded view, with the wrapper 28 and wrapper base 29 removed such as shown in FIG. 18. As can be seen, a first cover 25 and a second cover 27 are removably positioned to cover a pad 13 located on the first side 14 of the body 12. Openings 26 in both the first cover 25, and in the second cover 27 align with each other, and with respective reservoir areas 16 of the pad 13. The first cover 25 and second cover 27 are engaged to each other and to the first side 14 of the body 12 using removable adhesive such as adhesive type 9907HTW that is available from the 3M company.

In FIG. 13 is shown the deposit of liquid 38 through the aligned openings 26 communicating through both the first cover 25 and the second cover 27. The openings 26 form respective channels for the liquid 38 to be deposited and absorbed in the respective reservoir areas 16 which are aligned therewith.

In FIG. 14 is shown, the device of FIG. 12-13 with the removable first covering 25 and second covering 27 removed. As shown, the reservoir areas 16 are located on opposing sides of the mixing area 18. Adhesive is positioned on the first side 14 of the body 12.

Shown in FIG. 15 is a typical mode of a pad 13 used to form the plurality of reservoir areas 16 which is employable with all modes of the device 10 herein. The pad 13 is configured with a plurality of reservoir areas 16 located adjacent the mixing area 18. A membrane 24 such as a film or coating is positioned on the side of the pad 13 communicating with respective openings 26, which allows the liquid 38 to flow into the body of the pad 13, but substantially prevents any backflow. The liquid 38 in each respective reservoir area 16 flows along and through the fibers forming the pad 13 and into the mixing area 18 which is not covered by any membrane 24 and thereby communicates the mix to the skin of the user.

Figure 16:
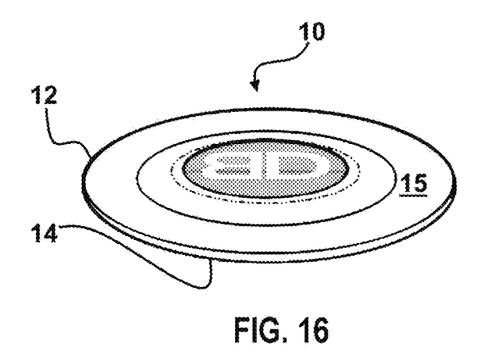
FIG. 16 depicts the device of FIGS. 12-15 in an as-used positioning where the second side is visible and the pad is in contact with the skin of a user.

The device as in FIGS. 12-15 is shown in FIG. 16, with the first cover 25 and second cover 27 disengaged, and ready for adherence to the skin of a user. As shown, the second side 15 of the body 12 would be exposed with adhesive located on the first side 14 of the body 12 holding the body 12 upon the user.

FIG. 17 shows another preferred mode of the device herein in an exploded view. As shown, the device 10 includes a body 12 having first body portion 30 connected by a hinge 32 or hinged engagement to a second body portion 31. The reservoir areas 16 are positioned on the first side 14 of the first body portion 30 in positions aligned with respective openings 26 which communicate through the first body portion 30. A separator 34 is located to cover adhesive 36 on the second body portion 31.

In FIG. 18 is depicted a removable wrapper formed of a wrapper cover 28 and wrapper base 29, which are adhesively or otherwise connected to form a cavity in which the device 10 is positioned prior to use. Such a removable wrapper may be employed with any of the disclosed modes of the device herein.

Figures 19, 20, 21, 22:
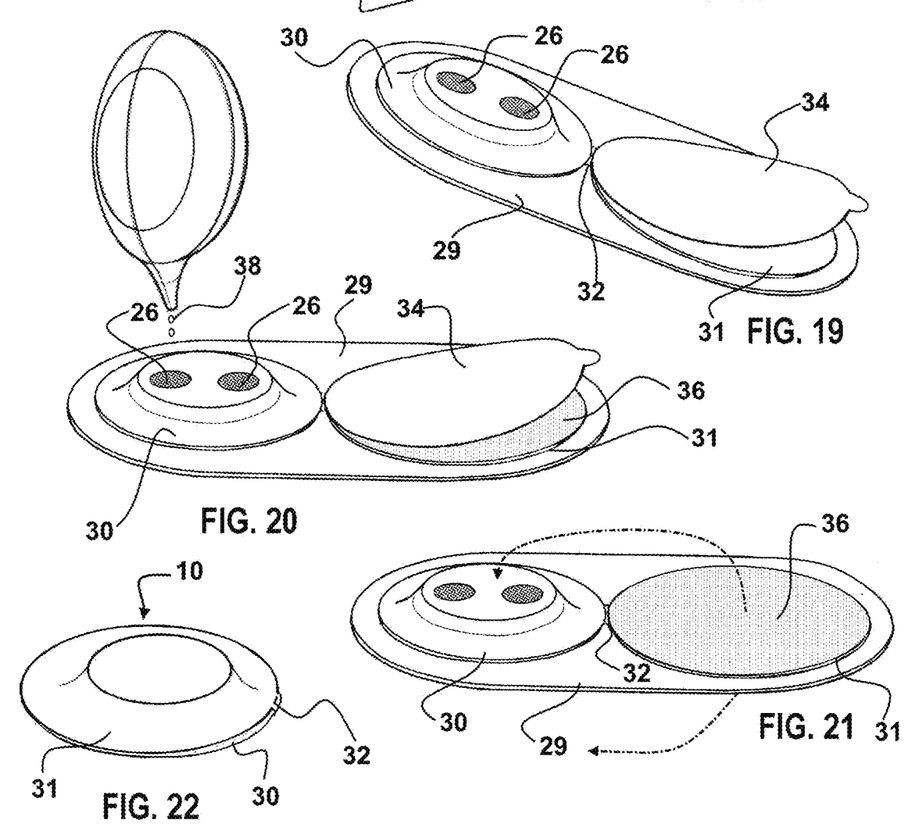
FIG. 19 depicts the device of FIG. 17 with the wrapper removed, showing the body formed of a first body portion in a hinged engagement to a second body portion and openings formed in the first body portion.
FIG. 20 depicts the deposit of liquid medication or oils or other liquid to the reservoir areas which each align with an opening that communicates through the first body portion.
FIG. 21 shows the device of FIG. 20 with a separator removed and how the second body portion is folded to engage the first body portion and removal of the holding layer from the first body portion.
FIG. 22 shows the device 10 formed of the second body portion covering the first body portion.
Figure 23:
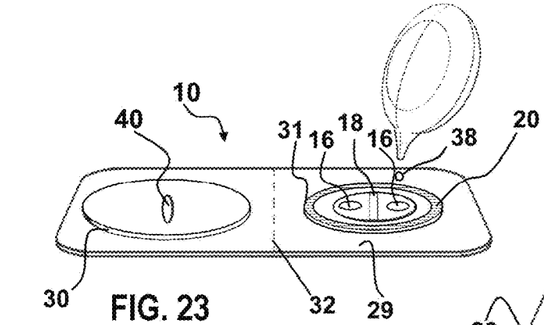
FIG. 23 shows another mode of the device herein formed of separate body portions with the wrapper removed.

In FIG. 19 is shown, the mode of device of FIG. 17 with the wrapper removed, or at least a wrapper cover 28 removed. As shown, the body is formable from a first body portion 30 which is in a hinged connection 32 to a second body portion 31. A separator 34 is removably positioned on the adhesive on the second body portion 31, which is used to connect the second body portion 31 to the first body portion 30. Both the first body portion 30 and second body portion 31 are removably located on a base which as shown is the wrapper base 29.

In FIGS. 20-21 is shown the typical deposit of liquid 38 medication or oils or other liquid 38 to the reservoir areas 16 which each align with an opening 26 that communicates through the first body portion 30 which may be formed of polymeric material in a conventional bandage fashion. Once the liquid 38 is communicated through each opening 26 which is aligned with a respective reservoir area 16, the separator 34 is dismounted as in FIG. 21, and the second body portion 31 is folded on the hinge 32 and engaged to the first body portion 30. This seals the openings 26, and forms the body from the adhesively engaged first body portion 30 and second body portion 31.

The result of the engagement of the first body portion 30 with the second body portion 31, is shown in FIG. 22, where the body 12 is formed from the two components and ready to be positioned on a user, with the openings 26 sealed by the second body portion 31.

FIGS. 23-28 show another mode of the bandage device 10 herein which is also formed from a first body portion 30 connected to a second body portion 31. As shown, the first body portion 30 is removably positioned on a base such as the wrapper base 29. The base has a pivot section or hinge 32 located in between the first body portion 30 and second body portion 31.

Figure 24:
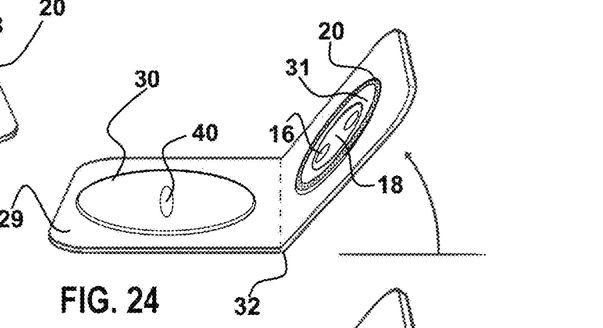
FIG. 24 shows a folding of a base to engage a second body portion having a pad forming reservoir areas to engage a first body portion having an opening aligned with a mixing area of the pad.
Figure 25:
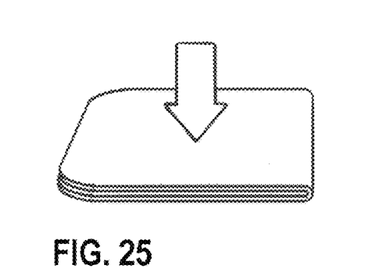
FIG. 25 depicts the folding of FIG. 24 completed.
Figure 26:
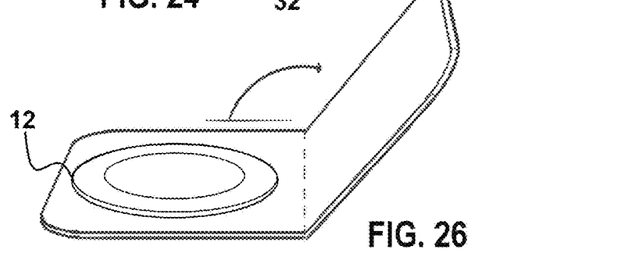
FIG. 26 depicts the unfolding of the base to show the device formed of the first body portion and second body portion and ready for positioning on the user.

Once the appropriate fluid has been deposited on the respective reservoir areas 16 of a pad or the like adhered to one side of the base, it is folded as in FIGS. 24-25, which causes the adhesive 20 on the second body portion 31 to adhere to the first body portion 30 when compressed as in FIG. 25. This forms the body of the device from the first body portion 30 and second body portion 31, and concurrently positions the mixing area 18 aligned with an aperture 40 formed through the first body portion 30.

Figure 27:
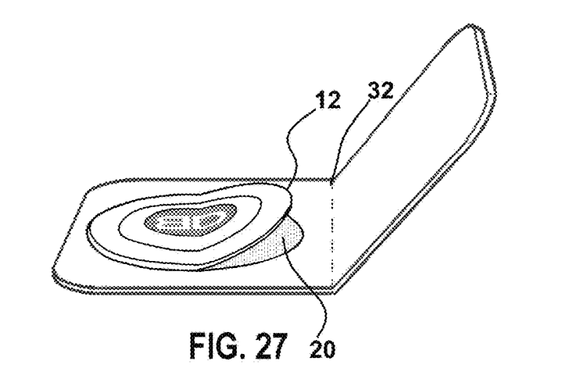
FIG. 27 shows removal of the first body portion from contact with a portion of the base so the device may be positioned on the skin of a user.
Figure 28:
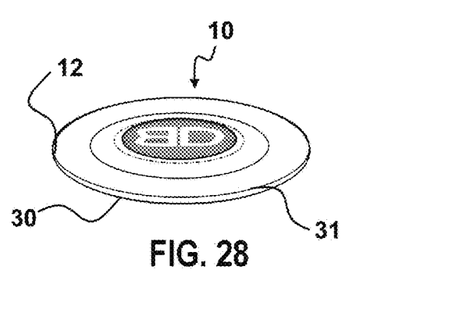
FIG. 28 depicts the device formed of the first body portion engaged to the second body portion wherein it is removed from the base.

The engaged body portions forming the body 12 of the device as in FIG. 27 may be removed from the adhesive 20 located on the base, and the device, as in FIG. 28, may be positioned on a user, wherein the mixed liquid in the mixing area 18 communicates through the aperture 40 to the skin of the user.

While the present invention has been described herein with reference to particular embodiments thereof and steps in the method of production and employment, a latitude of modifications, various changes and substitutions are intended in the foregoing disclosures, and it will be appreciated that in some instance some features, or configurations, or steps in formation and employment of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

Further, the purpose of any abstract of included with this specification is to enable the U.S. Patent and Trademark Office, the public generally, and especially the scientists, engineers, and practitioners in the art who are not familiar with patent or legal terms or phraseology, to determine quickly from a cursory inspection the nature and essence of the technical disclosure of the application. Any such abstract is neither intended to define the invention of the application, which is measured by the claims, nor is it intended to be limiting, as to the scope of the invention in any way.

The invention claimed is:

1. A bandage apparatus, comprising:
a flexible body having a first side surface opposite a second side surface;
adhesive located on said first side surface, said adhesive adapted to removably engage the flexible body to skin of a user;
a first reservoir area positioned on said first side surface of said flexible body, said first reservoir area for holding a first liquid topical treatment therein;
a second reservoir area positioned on said first side surface of said flexible body, said second reservoir area for holding a second liquid topical treatment therein;
a first mixing area on said first side surface of said flexible body, said first mixing area positioned between said first reservoir and said second reservoir;
a first fluid passage communicating said first liquid topical treatment from said first reservoir area mixing area to said first mixing area;
a second fluid passage communicating said second liquid topical treatment from said second reservoir area into said mixing area;
a removable first cover covering said first side surface;
a removable second cover covering said second side surface;
said first cover having a first opening and a second opening communicating therethrough;
said second cover having a first opening and a second opening communicating therethrough;
said first opening of said first cover being aligned with said first opening of said second cover to form a first passage in communication with said first reservoir area;
said second opening of said first cover being aligned with said second opening of said second cover to form a second passage in communication with said second reservoir area; and
whereby said first liquid topical treatment is communicable to said first reservoir area through said first passage and said second liquid topical treatment is communicable to said second reservoir area through said second passage and said first liquid topical treatment and said second liquid topical treatment communicated to said mixing area, combine therein to a first liquid mixture which communicates with skin of said user from said first mixing area.

2. The bandage apparatus of claim 1 further comprising:
an absorbent pad;
said first reservoir area positioned on a first side of said absorbent pad;
said second reservoir area positioned on a second side of said absorbent pad, opposite said first side;
said mixing area positioned on said absorbent pad in a central location in between said first reservoir area and said second reservoir area.

3. A bandage apparatus, comprising:
a flexible body having a first side surface opposite a second side surface;
adhesive located on said first side surface, said adhesive adapted to removably engage the flexible body to skin of a user;
a first reservoir area positioned on said first side surface of said flexible body, said first reservoir area for holding a first liquid topical treatment therein;
a second reservoir area positioned on said first side surface of said flexible body, said second reservoir area for holding a second liquid topical treatment therein;
a first mixing area on said first side surface of said flexible body, said first mixing area positioned between said first reservoir and said second reservoir;
a first fluid passage communicating said first liquid topical treatment from said first reservoir area mixing area to said first mixing area;
a second fluid passage communicating said second liquid topical treatment from said second reservoir area into said mixing area;
a first reservoir side edge running along a first side of said first mixing area;
a second reservoir side edge running along a second side of said first mixing area opposite said first side of said first mixing area;
said first fluid passage communicating into said mixing area through said first reservoir side edge; and
said second fluid passage communicating into said mixing area through said second reservoir side edge;
a removable first cover covering said first side edge;
a removable second cover covering said second side edge;
said first cover having a first opening and a second opening communicating therethrough;
said second cover having a first opening and a second opening communicating therethrough;
said first opening of said first cover being aligned with said first opening of said second cover to form a first passage in communication with said first reservoir area;
said second opening of said first cover being aligned with said second opening of said second cover to form a second passage in communication with said second reservoir area; and
whereby said first liquid topical treatment is communicable to said first reservoir area through said first passage and said second liquid topical treatment is communicable to said second reservoir area through said second passage.

4. The bandage apparatus of claim 3 further comprising:
an absorbent pad;
said first reservoir area positioned on a first side of said absorbent pad;
said second reservoir area positioned on a second side of said absorbent pad, opposite said first side;
said mixing area positioned on said absorbent pad in a central location in-between said first reservoir area and said second reservoir area.

5. A bandage apparatus, comprising:
a flexible body having a first side surface opposite a second side surface;
adhesive located on said first side surface, said adhesive adapted to removably engage the flexible body to skin of a user;
a first reservoir area positioned on said first side surface of said flexible body, said first reservoir area for holding a first liquid topical treatment therein;
a second reservoir area positioned on said first side surface of said flexible body, said second reservoir area for holding a second liquid topical treatment therein;
a first mixing area on said first side surface of said flexible body, said first mixing area positioned between said first reservoir and said second reservoir;
a first fluid passage communicating said first liquid topical treatment from said first reservoir area mixing area to said first mixing area;

a second fluid passage communicating said second liquid topical treatment from said second reservoir area into said mixing area;
wherein said first liquid topical treatment and said second liquid topical treatment communicated to said mixing area are combinable to a first liquid mixture for communication with skin of said user from said first mixing area;
said flexible body is formed of a first body portion in a hinged engagement to a second body portion;
a first opening communicating through said first body portion, said first opening being aligned with said first reservoir area;
a second opening communicating through said first body portion, said second opening being aligned with said second reservoir area;
adhesive positioned on a first side of said second body portion; and
said first side of said second body portion engageable to said first body portion to form a cover over both said first opening and said second opening.

6. A bandage apparatus, comprising:
a flexible body having a first side surface opposite a second side surface;
adhesive located on said first side surface, said adhesive adapted to removably engage the flexible body to skin of a user;
a first reservoir area positioned on said first side surface of said flexible body, said first reservoir area for holding a first liquid topical treatment therein;
a second reservoir area positioned on said first side surface of said flexible body, said second reservoir area for holding a second liquid topical treatment therein;
a first mixing area on said first side surface of said flexible body, said first mixing area positioned between said first reservoir and said second reservoir;
a first fluid passage communicating said first liquid topical treatment from said first reservoir area mixing area to said first mixing area;
a second fluid passage communicating said second liquid topical treatment from said second reservoir area into said mixing area;
wherein said first liquid topical treatment and said second liquid topical treatment communicated to said mixing area are combinable to a first liquid mixture for communication with skin of said user from said first mixing area;
a first reservoir side edge running along a first side of said first mixing area;
a second reservoir side edge running along a second side of said first mixing area opposite said first side of said first mixing area;
said first fluid passage communicating into said mixing area through said first reservoir side edge; and
said second fluid passage communicating into said mixing area through said second reservoir side edge;
said flexible body is formed of a first body portion in a hinged engagement to a second body portion;
a first opening communicating through said first body portion, said first opening being aligned with said first reservoir area;
a second opening communicating through said first body portion, said second opening being aligned with said second reservoir area;
adhesive positioned on a first side of said second body portion; and
said first side of said second body portion engageable to said first body portion to form a cover over both said first opening and said second opening.

7. A bandage apparatus, comprising:
a flexible body having a first side surface opposite a second side surface;
adhesive located on said first side surface, said adhesive adapted to removably engage the flexible body to skin of a user;
a first reservoir area positioned on said first side surface of said flexible body, said first reservoir area for holding a first liquid topical treatment therein;
a second reservoir area positioned on said first side surface of said flexible body, said second reservoir area for holding a second liquid topical treatment therein;
a first mixing area on said first side surface of said flexible body, said first mixing area positioned between said first reservoir and said second reservoir;
a first fluid passage communicating said first liquid topical treatment from said first reservoir area mixing area to said first mixing area;
a second fluid passage communicating said second liquid topical treatment from said second reservoir area into said mixing area;
wherein said first liquid topical treatment and said second liquid topical treatment communicated to said mixing area are combinable to a first liquid mixture for communication with skin of said user from said first mixing area;
an absorbent pad;
said first reservoir area positioned on a first side of said absorbent pad;
said second reservoir area positioned on a second side of said absorbent pad, opposite said first side;
said mixing area positioned on said absorbent pad in a central location in between said first reservoir area and said second reservoir area;
said flexible body is formed of a first body portion in a hinged engagement to a second body portion;
a first opening communicating through said first body portion, said first opening being aligned with said first reservoir area;
a second opening communicating through said first body portion, said second opening being aligned with said second reservoir area;
adhesive positioned on a first side of said second body portion; and
said first side of said second body portion engageable to said first body portion to form a cover over both said first opening and said second opening.

8. A bandage apparatus, comprising:
a flexible body having a first side surface opposite a second side surface;
adhesive located on said first side surface, said adhesive adapted to removably engage the flexible body to skin of a user;
a first reservoir area positioned on said first side surface of said flexible body, said first reservoir area for holding a first liquid topical treatment therein;
a second reservoir area positioned on said first side surface of said flexible body, said second reservoir area for holding a second liquid topical treatment therein;
a first mixing area on said first side surface of said flexible body, said first mixing area positioned between said first reservoir and said second reservoir;

a first fluid passage communicating said first liquid topical treatment from said first reservoir area mixing area to said first mixing area;
a second fluid passage communicating said second liquid topical treatment from said second reservoir area into said mixing area;
a first reservoir side edge running along a first side of said first mixing area;
a second reservoir side edge running along a second side of said first mixing area opposite said first side of said first mixing area;
said first fluid passage communicating into said mixing area through said first reservoir side edge; and
said second fluid passage communicating into said mixing area through said second reservoir side edge;
an absorbent pad;
said first reservoir area positioned on a first side of said absorbent pad;
said second reservoir area positioned on a second side of said absorbent pad, opposite said first side;
said mixing area positioned on said absorbent pad in a central location in-between said first reservoir area and said second reservoir area;
said flexible body is formed of a first body portion in a hinged engagement to a second body portion;
a first opening communicating through said first body portion, said first opening being aligned with said first reservoir area;
a second opening communicating through said first body portion, said second opening being aligned with said second reservoir area;
adhesive positioned on a first side of said second body portion; and
said first side of said second body portion engageable to said first body portion to form a cover over both said first opening and said second opening.

9. A bandage apparatus, comprising:
a flexible body having a first side surface opposite a second side surface;
adhesive located on said first side surface, said adhesive adapted to removably engage the flexible body to skin of a user;
a first reservoir area positioned on said first side surface of said flexible body, said first reservoir area for holding a first liquid topical treatment therein;
a second reservoir area positioned on said first side surface of said flexible body, said second reservoir area for holding a second liquid topical treatment therein;
a first mixing area on said first side surface of said flexible body, said first mixing area positioned between said first reservoir and said second reservoir;
a first fluid passage communicating said first liquid topical treatment from said first reservoir area mixing area to said first mixing area;
a second fluid passage communicating said second liquid topical treatment from said second reservoir area into said mixing area;
wherein said first liquid topical treatment and said second liquid topical treatment communicated to said mixing area are combinable to a first liquid mixture for communication with skin of said user from said first mixing area;
an absorbent pad;
said first reservoir area positioned on a first side of said absorbent pad;
said second reservoir area positioned on a second side of said absorbent pad, opposite said first side;
said mixing area positioned on said absorbent pad in a central location in between said first reservoir area and said second reservoir area;
said flexible body is formed of a first body portion and a second body portion;
said first body portion removably positioned on a first side of a base;
said second body portion removably positioned on a second side of a base;
said pad engaged to said second body portion;
adhesive positioned on said second body portion;
said second body portion engageable in an aligned engagement to said first body portion, by a folding of said base along a hinged area thereof; and
an aperture communicating through said first body portion, said aperture aligned with said mixing area with said second body portion in said aligned engagement with said first body portion.

10. A bandage apparatus, comprising:
a flexible body having a first side surface opposite a second side surface;
adhesive located on said first side surface, said adhesive adapted to removably engage the flexible body to skin of a user;
a first reservoir area positioned on said first side surface of said flexible body, said first reservoir area for holding a first liquid topical treatment therein;
a second reservoir area positioned on said first side surface of said flexible body, said second reservoir area for holding a second liquid topical treatment therein;
a first mixing area on said first side surface of said flexible body, said first mixing area positioned between said first reservoir and said second reservoir;
a first fluid passage communicating said first liquid topical treatment from said first reservoir area mixing area to said first mixing area;
a second fluid passage communicating said second liquid topical treatment from said second reservoir area into said mixing area;
a first reservoir side edge running along a first side of said first mixing area;
a second reservoir side edge running along a second side of said first mixing area opposite said first side of said first mixing area;
said first fluid passage communicating into said mixing area through said first reservoir side edge; and
said second fluid passage communicating into said mixing area through said second reservoir side edge;
an absorbent pad;
said first reservoir area positioned on a first side of said absorbent pad;
said second reservoir area positioned on a second side of said absorbent pad, opposite said first side;
said mixing area positioned on said absorbent pad in a central location in-between said first reservoir area and said second reservoir area;
said flexible body is formed of a first body portion and a second body portion;
said first body portion removably positioned on a first side of a base;
said second body portion removably positioned on a second side of a base;
said pad engaged to said second body portion;
adhesive positioned on said second body portion;
said second body portion engageable in an aligned engagement to said first body portion, by a folding of said base along a hinged area thereof; and an aperture communicating through said first body portion, said aperture aligned with said mixing area with said second body portion in said aligned engagement with said first body portion.

* * * * *